(12) United States Patent
Burnett, Jr. et al.

(10) Patent No.: US 7,803,901 B2
(45) Date of Patent: Sep. 28, 2010

(54) POLYPEPTIDES WITH NATRIURESIS ACTIVITY

(75) Inventors: John C. Burnett, Jr., Rochester, MN (US); Timothy M. Olson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/065,673

(22) PCT Filed: Sep. 15, 2006

(86) PCT No.: PCT/US2006/036227
§ 371 (c)(1),
(2), (4) Date: Sep. 16, 2008

(87) PCT Pub. No.: WO2007/035600
PCT Pub. Date: Mar. 29, 2007

(65) Prior Publication Data
US 2009/0069243 A1    Mar. 12, 2009

Related U.S. Application Data

(60) Provisional application No. 60/717,655, filed on Sep. 16, 2005.

(51) Int. Cl.
*C07K 14/00* (2006.01)
*A61K 38/17* (2006.01)

(52) U.S. Cl. .......................... 530/324; 514/2
(58) Field of Classification Search ........................ None
See application file for complete search history.

(56) References Cited

U.S. PATENT DOCUMENTS

| | | | |
|---|---|---|---|
| 4,161,521 A | 7/1979 | Veber et al. | |
| 4,683,195 A | 7/1987 | Mullis et al. | |
| 5,580,859 A | 12/1996 | Felgner et al. | |
| 5,589,466 A | 12/1996 | Felgner et al. | |
| 6,013,630 A | 1/2000 | Shimkets | |
| 6,407,211 B1 * | 6/2002 | Burnett et al. | 530/350 |
| 6,818,619 B2 | 11/2004 | Burnett, Jr. et al. | |
| 6,833,447 B1 * | 12/2004 | Goldman et al. | 536/23.1 |
| 7,276,481 B2 * | 10/2007 | Golembo et al. | 514/13 |
| 7,345,142 B2 | 3/2008 | Cohen et al. | |

FOREIGN PATENT DOCUMENTS

| | | | |
|---|---|---|---|
| WO | WO 2004/047871 | | 6/2004 |
| WO | WO/2004/047871 | * | 6/2004 |

OTHER PUBLICATIONS

Vesely DL, Atrial natriuretic peptides in pathophysiological diseases, Cardiovascular research, 51, 647-658, 2001;.*
Vesely DL, Natriuretic peptides and acute renal failure, Am. J. Physiol. Renal.Physiol. 285: F167-F177, 2003.*
PubMed search for atrial natriuretic peptide;Nov. 24, 2009.*
PubMed search for brain natriuretic peptide;Nov. 24, 2009.*
PubMed search for C-type natriuretic peptide;Nov. 24, 2009.*
PubMed search for DNP;Nov. 24, 2009.*
PubMed search for Salmon natriuretic peptide;Nov. 24, 2009.*
GenBank Accession No. BC005893, dated Jul. 15, 2006, 3 pgs.
Lebl and Hruby, "Synthesis of Cyclic Peptides by Solid Phase Methodology," *Tetrahedron Letters*, 1984, 25(20):2067-2068.
Burnett et al., "Atrial Natriuretic Peptide Elevation in Congestive Heart failure in the Human," Science, *Science*, 1986, 231:1145-1147.

* cited by examiner

*Primary Examiner*—Christine J Saoud
*Assistant Examiner*—Elly-Gerald Stoica
(74) *Attorney, Agent, or Firm*—Fish & Richardson P.C.

(57) ABSTRACT

This document provides methods and material related to natriuretic polypeptides. For example, substantially pure polypeptides having a natriuretic peptide activity, nucleic acids encoding polypeptides having a natriuretic peptide activity, host cells containing such nucleic acids, and methods for inducing a natriuretic or diuretic activity within a mammal are provided.

9 Claims, 7 Drawing Sheets

POLYPEPTIDES WITH NATRIURESIS ACTIVITY

CROSS-REFERENCE TO RELATED APPLICATIONS

This application is a National Stage application under 35 U.S.C. §371 and claims benefit under 35 U.S.C. §119(a) of International Application No. PCT/US2006/036227 having an International Filing Date of Sep. 15, 2006, which claims the benefit of priority of U.S. Provisional Application Ser. No. 60/717,655 having a filing date of Sep. 16, 2005.

BACKGROUND

1. Technical Field

This document relates to methods and materials involved in inducing natriuretic or diuretic activity.

2. Background Information

Natriuretic polypeptides are polypeptides that can cause natriuresis (e.g., excretion of an excessively large amount of sodium in the urine). Such polypeptides can be produced by brain, heart, and/or vasculature tissue.

SUMMARY

This document provides methods and material related to natriuretic polypeptides. For example, this document provides substantially pure polypeptides having a natriuretic peptide activity, nucleic acids encoding polypeptides having a natriuretic peptide activity, host cells containing such nucleic acids, and methods for inducing a natriuretic or diuretic activity within a mammal.

In general, one aspect of this document features a substantially pure polypeptide comprising, or consisting essentially of, an amino acid sequence as set forth in SEQ ID NO:1, or an amino acid sequence as set forth in SEQ ID NO:1 having less than five amino acid additions, subtractions, and substitutions. The polypeptide can comprise an amino acid sequence present in an ANP polypeptide. The polypeptide can comprise an amino acid sequence present in a BNP polypeptide. The polypeptide can comprise an amino acid sequence present in an CNP polypeptide. The polypeptide can comprise an amino acid sequence present in an DNP polypeptide. The polypeptide can comprise an amino acid sequence present in a salmon natriuretic factor polypeptide. The polypeptide can comprise the amino acid sequence as set forth in SEQ ID NO:1. The polypeptide can comprise the amino acid sequence as set forth in SEQ ID NO:1 having less than five amino acid additions, subtractions, and substitutions. The polypeptide can comprise the amino acid sequence as set forth in SEQ ID NO:1 having less than four amino acid additions, subtractions, and substitutions.

In another aspect, this document features an isolated nucleic acid comprising, or consisting essentially of, a nucleotide sequence encoding an amino acid sequence as set forth in SEQ ID NO:1, or an amino acid sequence as set forth in SEQ ID NO:1 having less than five amino acid additions, subtractions, and substitutions. The nucleic acid can encode an amino acid sequence present in an ANP polypeptide. The nucleic acid can encode an amino acid sequence present in a BNP polypeptide. The nucleic acid can encode an amino acid sequence present in an CNP polypeptide. The nucleic acid can encode an amino acid sequence present in an DNP polypeptide. The nucleic acid can encode an amino acid sequence present in a salmon natriuretic factor polypeptide. The nucleotide sequence can encode the amino acid sequence as set forth in SEQ ID NO:1. The nucleotide sequence can encode the amino acid sequence as set forth in SEQ ID NO:1 having less than five amino acid additions, subtractions, and substitutions. The nucleotide sequence can encode the amino acid sequence as set forth in SEQ ID NO:1 having less than four amino acid additions, subtractions, and substitutions.

In another aspect, this document features a host cell comprising, or consisting essentially of, an exogenous nucleic acid comprising a nucleotide sequence encoding an amino acid sequence as set forth in SEQ ID NO:1, or an amino acid sequence as set forth in SEQ ID NO:1 having less than five amino acid additions, subtractions, and substitutions.

In another aspect, this document features a method for inducing a natriuretic or diuretic action in a mammal. The method comprises, or consists essentially of, administering to the mammal a polypeptide comprising an amino acid sequence as set forth in SEQ ID NO:1, or an amino acid sequence as set forth in SEQ ID NO:1 having less than five amino acid additions, subtractions, and substitutions.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials related to natriuretic polypeptides. For example, this document provides substantially pure polypeptides having a natriuretic polypeptide activity, nucleic acid molecules encoding polypeptides having a natriuretic polypeptide activity, and host cells containing isolated nucleic acid molecules that encode polypeptides having a natriuretic polypeptide activity. In addition, this document provides methods and materials for inducing a natriuretic or diuretic activity within a mammal.

The term "substantially pure" as used herein with reference to a polypeptide means the polypeptide is substantially free of other polypeptides, lipids, carbohydrates, and nucleic acid with which it is naturally associated. A substantially pure polypeptide can be any polypeptide that is removed from its natural environment and is at least 60 percent pure. A substantially pure polypeptide can be at least about 65, 70, 75, 80, 85, 90, 95, or 99 percent pure. Typically, a substantially pure polypeptide will yield a single major band on a non-reducing polyacrylamide gel. A substantially pure polypeptide can be a chemically synthesized polypeptide.

Any method can be used to obtain a substantially pure polypeptide. For example, common polypeptide purification techniques such as affinity chromatography and HPLC as well as polypeptide synthesis techniques can be used. In addition, any material can be used as a source to obtain a substantially pure polypeptide. For example, tissue from wild-type or transgenic animals can be used as a source material. In addition, tissue culture cells engineered to over-express a particular polypeptide can be used to obtain substantially pure polypeptide. Further, a polypeptide can be engineered to contain an amino acid sequence that allows the polypeptide to be captured onto an affinity matrix. For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini, or in between. Other fusions that can be used include enzymes that aid in the detection of the polypeptide, such as alkaline phosphatase.

The polypeptides provided herein can contain the entire amino acid sequence set forth in SEQ ID NO:1. In some cases, a polypeptide can contain the amino acid sequence set forth in SEQ ID NO:1 except that the amino acid sequence contains one or between one and ten (e.g., between one and nine, one and eight, between one and seven, between one and six, between one and five, between one and four, between one and three, or two) amino acid additions, subtractions, and substitutions. For example, a polypeptide can contain the amino acid sequence set forth in SEQ ID NO:1 with one, two, three, four, five, six, seven, eight, nine, or ten single amino acid residue additions, subtractions, or substitutions. An example of such a polypeptide includes, without limitation, a polypeptide having the amino acid sequence set forth in SEQ ID NO:1 where the threonine is deleted, the tryptophan is replaced with a tyrosine, and a serine is added between the lysine and the glutamine. Another example can be a polypeptide containing a contiguous amino acid sequence that is identical to the first eight amino acid residues set forth in SEQ ID NO:1 and lacking last three residues (i.e., glycine, tryptophan, and alanine).

Any amino acid residue set forth in SEQ ID NO:1 can be subtracted, and any amino acid residue (e.g., any of the 20 conventional amino acid residues or any other type of amino acid such as ornithine or citrulline) can be added to the sequence set forth in SEQ ID NO:1. In some cases, a polypeptide provided herein can contain chemical structures such as ε-aminohexanoic acid; hydroxylated amino acids such as 3-hydroxyproline, 4-hydroxyproline, (5R)-5-hydroxy-L-lysine, allo-hydroxylysine, and 5-hydroxy-L-norvaline; or glycosylated amino acids such as amino acids containing monosaccharides (e.g., D-glucose, D-galactose, D-mannose, D-glucosamine, and D-galactosamine) or combinations of monosaccharides.

Polypeptides having one or more amino acid substitutions relative to a native polypeptide can be prepared and modified as described herein. Amino acid substitutions can be conservative amino acid substitutions. Conservative amino acid substitutions are, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide.

In some cases, amino acid substitutions can be substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic; trp, tyr, phe. In some cases, non-conservative substitutions can be used. A non-conservative substitution can include exchanging a member of one of the classes described herein for another.

In some cases, a polypeptide provided herein can be pegylated, acetylated, or both. In some cases, a polypeptide provided herein can be covalently attached to oligomers, such as short, amphiphilic oligomers that enable oral administration or improve the pharmacokinetic or pharmacodynamic profile of the conjugated polypeptide. The oligomers can comprise water soluble polyethylene glycol (PEG) and lipid soluble alkyls (short chain fatty acid polymers). See, for example, International Patent Application Publication No. WO 2004/047871. In some cases, a polypeptide provided herein can be fused to the Fc domain of an immunoglobulin molecule (e.g., an IgG1 molecule) such that active transport of the fusion polypeptide across epithelial cell barriers occurs via the Fc receptor. In some cases, a polypeptide can be a cyclic polypeptide. A cyclic polypeptide provided herein can be obtained by bonding cysteine residues, however, the replacement of a sulfhydryl group on the cysteine residue with an alternative group is also envisioned, for example, —CH$_2$—CH$_2$—. For example, to replace sulfhydryl groups with a —CH$_2$— group, the cysteine residues can be replaced by the analogous alpha-aminobutyric acid. These cyclic analog peptides can be formed, for example, in accordance with the methodology of Lebl and Hruby (1984), or by employing the procedure disclosed in U.S. Pat. No. 4,161,521.

A substantially pure polypeptide provided herein can contain one or more sequences present in a polypeptide having natriuretic polypeptide activity. Examples of polypeptides having a natriuretic polypeptide activity (e.g., an atrial natriuretic peptide (ANP) activity) include, without limitation, brain natriuretic peptide (BNP), C-type natriuretic peptide (CNP), urodilatin, snake natriuretic peptide (DNP), and ANP polypeptides. The polypeptides having a natriuretic polypeptide activity can have a non-naturally occurring sequence or can have a sequence present in any species (e.g., human, horse, pig, goat, cow, dog, cat, rat, or mouse). For example, a polypeptide having a natriuretic polypeptide activity can be a human ANP polypeptide having one or more amino acid changes. In some cases, a polypeptide having natriuretic polypeptide activity can be a human ANP polypeptide. For example, a polypeptide provided herein can contain the amino acid sequence of ANP followed by the amino acid sequence set forth in SEQ ID NO:1, or the amino acid sequence set forth in SEQ ID NO:1 except that the amino acid sequence contains one or between one and ten amino acid additions, subtractions, and substitutions. An example of such a polypeptide can be the LA-ANP polypeptide provided herein.

A substantially pure polypeptide provided herein can have a natriuretic peptide activity. For example, a polypeptide provided herein can have natriuretic or diuretic activity. Any method can be use to determine whether or not a particular polypeptide has a natriuretic peptide activity. For example, a mammal (e.g., dog or human) exposed to a particular polypeptide can be analyzed to determine the polypeptide's ability to induce natriuretic or diuretic activity.

This document also provides nucleic acid molecules having a sequence that encodes any of the polypeptides provided herein. For example, this document provides nucleic acid molecules that encode a natriuretic peptide containing the amino acid sequence set forth in SEQ ID NO:1. In some cases, a nucleic acid molecule provided herein can encode a polypeptide that contains the amino acid sequence set forth in SEQ ID NO:1 except that the amino acid sequence contains one or between one and ten (e.g., between one and nine, one and eight, between one and seven, between one and six, between one and five, between one and four, between one and three, or two) amino acid additions, subtractions, and substitutions as described herein.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

In some cases, an isolated nucleic acid molecules provided herein can be at least about 12 bases in length (e.g., at least about 13, 14, 15, 16, 17, 18, 19, 20, 25, 30, 40, 50, 60, 100, 250, 500, 750, 1000, 1500, 2000, 3000, 4000, or 5000 bases in length) and hybridize, under hybridization conditions, to the sense or antisense strand of a nucleic acid having a sequence that encodes the sequence set forth in SEQ ID NO:1. The hybridization conditions can be moderately or highly stringent hybridization conditions. In some cases, such nucleic acid molecules can be molecules that do not hybridize to the sense or antisense strand of a nucleic acid that consists only of the coding sequence of a natriuretic peptide such as human ANP, human BNP, or human CNP.

For the purpose of this document, moderately stringent hybridization conditions mean the hybridization is performed at about 42° C. in a hybridization solution containing 25 mM $KPO_4$ (pH 7.4), 5×SSC, 5×Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM $KPO_4$ (pH 7.4), 5×SSC, 5×Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 65° C. with a wash solution containing 0.2×SSC and 0.1% sodium dodecyl sulfate.

An isolated nucleic acid molecule provided herein can be obtained using any method including, without limitation, common molecular cloning and chemical nucleic acid synthesis techniques. For example, PCR can be used to obtain an isolated nucleic acid molecule containing a nucleic acid sequence sharing similarity to sequences that encode the amino acid sequence set forth in SEQ ID NO:1. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complementary DNA strands.

An isolated nucleic acid molecule provided herein can be obtained by mutagenesis. For example, an isolated nucleic acid containing a sequence that encodes the amino acid sequence set forth in SEQ ID NO:1 can be mutated using common molecular cloning techniques (e.g., site-directed mutagenesis). Possible mutations include, without limitation, additions, subtractions, and substitutions, as well as combinations of additions, subtractions, and substitutions.

This document also provides host cells containing at least one of the isolated nucleic acid molecules provided herein. Such cells can be prokaryotic and eukaryotic cells. It is noted that cells containing an isolated nucleic acid molecule provided herein are not required to express a polypeptide. In addition, the isolated nucleic acid molecule can be integrated into the genome of the cell or maintained in an episomal state. Thus, host cells can be stably or transiently transfected with a construct containing an isolated nucleic acid molecule provided herein.

Host cells can contain an exogenous nucleic acid molecule that encodes a polypeptide provided herein (e.g., a polypeptide containing an amino acid sequence as set forth in SEQ ID NO: 1). Such host cells can express the encoded polypeptide.

Any methods can be used to introduce an isolated nucleic acid molecule into a cell in vivo or in vitro. For example, calcium phosphate precipitation, electroporation, heat shock, lipofection, microinjection, and viral-mediated nucleic acid transfer are common methods that can be used to introduce an isolated nucleic acid molecule into a cell. In addition, naked DNA can be delivered directly to cells in vivo as describe elsewhere (U.S. Pat. No. 5,580,859 and U.S. Pat. No. 5,589,466 including continuations thereof). Further, isolated nucleic acid molecules can be introduced into cells by generating transgenic animals.

Any methods can be used to identify cells containing an isolated nucleic acid molecule provided herein. Such methods include, without limitation, PCR and nucleic acid hybridization techniques such as Northern and Southern analysis. In some cases, immunohistochemistry and biochemical techniques can be used to determine if a cell contains a particular isolated nucleic acid molecule by detecting the expression of a polypeptide encoded by that particular nucleic acid molecule.

As described herein, the polypeptides provided herein as well as compositions containing one or more of such polypeptides can be used to induce a natriuretic or diuretic activity in a mammal. Any route of administration (e.g., oral or parenteral administration) can be used to administer a polypeptide or composition provided herein (e.g., a composition containing one or more of the polypeptides provided herein) to a mammal. For example, a composition can be administered orally or parenterally (e.g., a subcutaneous, intramuscular, intraorbital, intracapsular, intraspinal, intrasternal, or intravenous injection). Compositions containing a polypeptide provided herein can contain additional ingredients such as those described in U.S. Pat. No. 6,818,619. Such additional ingredients can be polypeptides or non-polypeptides (e.g., buffers). In addition, the polypeptides within a composition provided herein can be in any form such as those described in U.S. Pat. No. 6,818,619.

Before administering a composition provided herein to a mammal, the mammal can be assessed to determine whether or not the mammal has a need for increased natriuretic or diuretic activity (e.g., a patient having a sodium retention disorder). After identifying a mammal as having a need for increased natriuretic or diuretic activity, the mammal can be treated with a composition provided herein. For example, a composition containing one or more polypeptides having a natriuretic polypeptide activity can be administered to a mammal in any amount, at any frequency, and for any duration effective to achieve a desired outcome (e.g., to increase renal function).

An effective amount of a composition can be any amount that increases natriuretic or diuretic activity within a mammal without producing significant toxicity to the mammal. If a particular mammal fails to respond to a particular amount, then the amount can be increased by, for example, ten fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment.

The frequency of administration can be any frequency that increases natriuretic or diuretic activity within a mammal without producing significant toxicity to the mammal. For example, the frequency of administration can be from about four times a day to about once every other month, or from about once a day to about once a month, or from about once every other day to about once a week. In addition, the frequency of administration can remain constant or can be variable during the duration of treatment. As with the effective amount, various factors can influence the actual frequency of administration used for a particular application. For example, the effective amount, duration of treatment, route of administration, and severity of renal condition may require an increase or decrease in administration frequency.

An effective duration of administration can be any duration that increases natriuretic or diuretic activity within a mammal without producing significant toxicity to the mammal. The effective duration can vary from several days to several weeks, months, or years. In general, the effective duration for increasing natriuretic or diuretic activity can range in duration from several days to several months. Typically, an effective duration can range from about one to two weeks to about 36 months. Prophylactic treatments can be typically longer in duration and can last throughout an individual mammal's lifetime.

Multiple factors can influence the actual effective duration used for a particular treatment or prevention regimen. For example, an effective duration can vary with the frequency of administration, amount administered, route of administration, and severity of a renal condition.

After administering a composition provided herein to a mammal, the mammal can be monitored to determine whether or not renal function has been improved. For example, a mammal can be assessed after treatment to determine whether or not renal function increased. As described herein, any method can be used to assess improvements in renal function.

After administering a composition provided herein to a mammal, the mammal also can be monitored to determine the serum level of a polypeptide provided herein. Any appropriate method can be used to measure serum levels of a polypeptide provided herein including, without limitation, mass spectrometry and immunological methods such as ELISA. An antibody used in an immunological assay can be, without limitation, a polyclonal, monoclonal, human, humanized, chimeric, or single-chain antibody, or an antibody fragment having binding activity, such as a Fab fragment, F(ab') fragment, Fd fragment, fragment produced by a Fab expression library, fragment comprising a VL or VH domain, or epitope binding fragment of any of the above. An antibody can be of any type, (e.g., IgG, IgM, IgD, IgA or IgY), class (e.g., IgG1, IgG4, or IgA2), or subclass. In addition, an antibody can be from any animal including birds and mammals. For example, an antibody can be a human, rabbit, sheep, or goat antibody. Such an antibody can be capable of binding specifically to a polypeptide provided herein.

Antibodies can be generated and purified using any suitable methods known in the art. For example, monoclonal antibodies can be prepared using hybridoma, recombinant, or phage display technology, or a combination of such techniques. In some cases, antibody fragments can be produced synthetically or recombinantly from a gene encoding the partial antibody sequence. In some cases, an antibody fragment can be enzymatically or chemically produced by fragmentation of an intact antibody. An antibody directed against a polypeptide provided herein can bind the polypeptide at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$).

The invention will be further described in the following examples, which do not limit the scope of the invention described in the claims.

EXAMPLES

Example 1

Hemodynamic and Renal Properties of Long-Acting ANP

Figure 1:
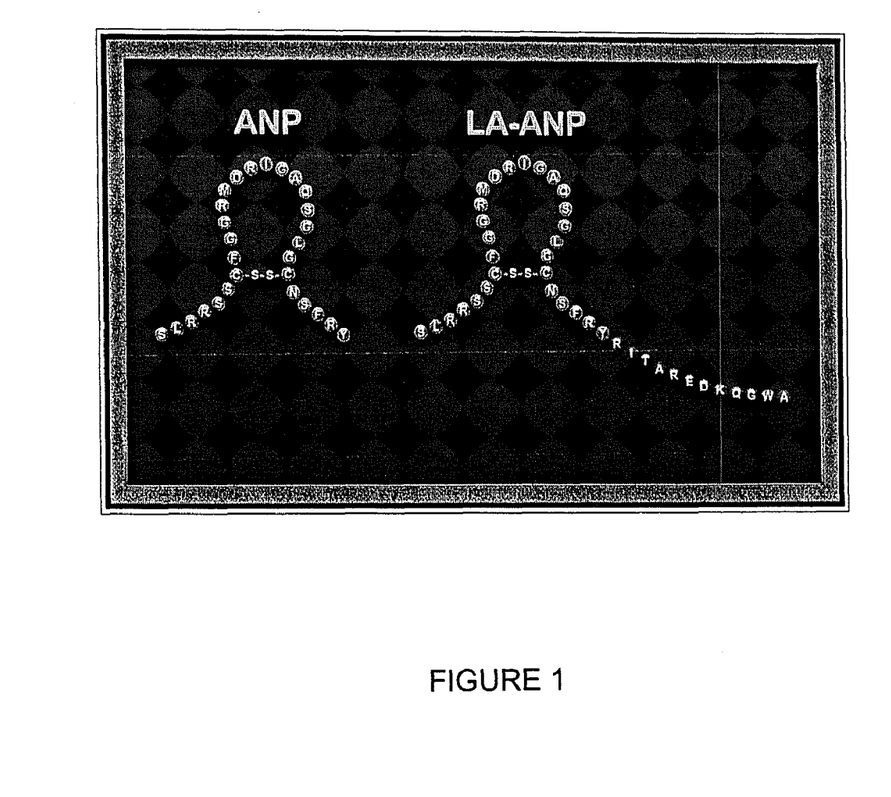
FIG. 1 is graphical representation of ANP and LA-ANP.

A long-acting atrial natriuretic peptide (LA-ANP) having the 28 amino acid ANP peptide with an additional 12 amino acid carboxy terminus was obtained. The amino acid sequence of the additional 12 amino acid carboxy terminus of LA-ANP was as follows: RITAREDKQGWA (SEQ ID NO:1). The full length sequence of LA-ANP was as follows: SLRRSSCFGGRMDRIGAQSGLGCNS-FRYRITAREDKQGWA (SEQ ID NO:2). The amino acid sequence of a mature form of human atrial natriuretic peptide is SLRRSSCFGGRMDRIGAQSGLGCNSFRY (SEQ ID NO:3). The following nucleic acid sequence can encode human ANP: 5'-agcctgcggagatccagctgct-tcgggggcaggatggacaggattggagc-ccagagcggactgggctgtaacagcttccggtacc gaagataa-3' (SEQ ID NO:4) The C-terminal Y of human ANP can be removed in some cases. Also, human ANP can contain a YRR sequence in place of the C-terminal Y of SEQ ID NO:1. The following nucleic acid sequence encodes LA-ANP:

(SEQ ID NO: 5)
5'-agcctgcggagatccagctgcttcgggggcaggatggacaggattgg agcccagagcggactgggctgtaacag-cttccggtaccggataacagcc agggaggacaagcagggctgggcctag-3'.

Studies comparing LA-ANP to ANP were performed in normal dogs that were anesthetized. Equimolar concentrations of a low dose (2 pmol/kg/min) of LA-ANP and ANP were infused intravenously, where ANP was administered at a threshold concentration required to activate cyclic guanosine monophosphate. Equimolar concentrations of a high dose of LA-ANP and ANP (33 pmol/kg/min.) were also infused intravenously. Infusion of ANP or LA-ANP for 45 minutes was performed following a 30 minute baseline period, which was preceded by a 60 minute equilibrium period. Infusion was followed by a 30 minute wash-out period and three recovery (Rec) periods of 30 minutes each. Hemodynamic and renal parameters were measured at baseline (BL), during 45 minutes of infusion, and 120 minutes post-infusion.

Figure 2:
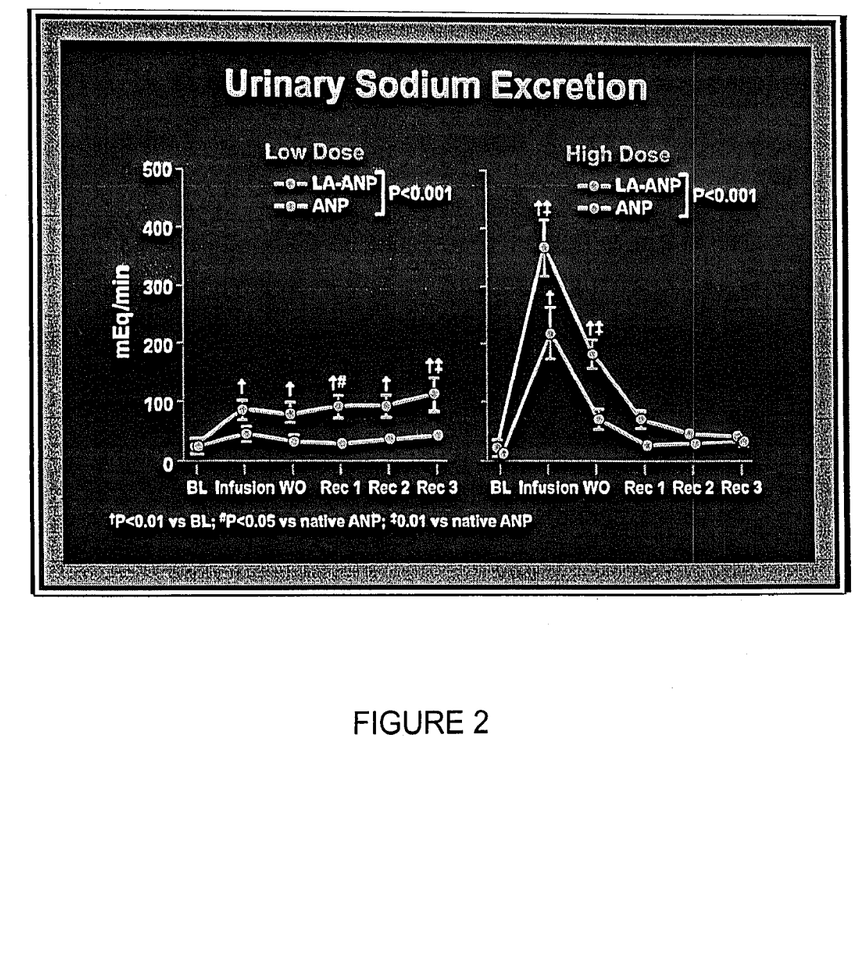
FIG. 2 is a graph plotting urinary sodium excretion at the indicated time points for animals receiving ANP or LA-ANP.
Figure 3:
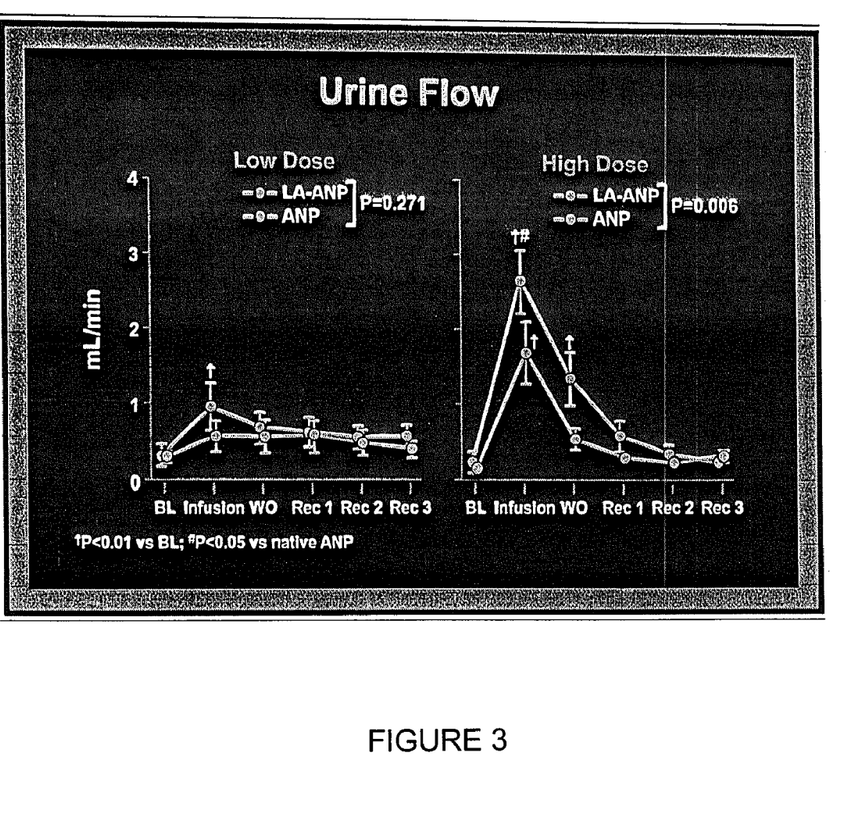
FIG. 3 is a graph plotting urine flow at the indicated time points for animals receiving ANP or LA-ANP.

LA-ANP produced both a greater diuretic effect and a greater natriuretic effect as compared to ANP. Natriuresis was not increased during infusion of a low dose of ANP or at 120 minutes post-infusion of a low dose of ANP. In contrast, a low dose of LA-ANP significantly increased urinary sodium excretion from 47.0±18.9 µEq/min. at baseline to 88.4±17.5 µEq/min. during infusion (p<0.01), and to 119.2±34.2 µEq/min. at 120 minutes post-infusion (p<0.01). Similar to the observed lack of an effect of a low dose of ANP on natriuresis, there was no significant change in diuresis with infusion of a low dose of ANP. Diuresis was, however, observed to increase in response to infusion of a low dose of LA-ANP, from 0.34±0.08 mL/min. at baseline to 1.08±0.23 mL/min. during infusion (p<0.01).

Figure 4:
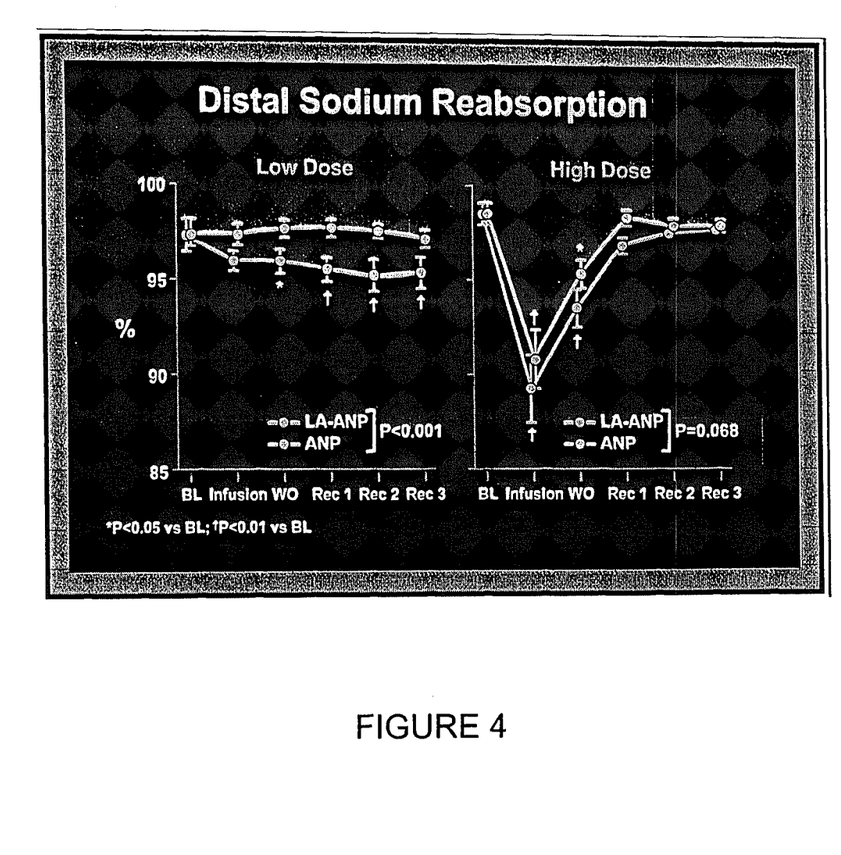
FIG. 4 is a graph plotting distal sodium reabsorption at the indicated time points for animals receiving ANP or LA-ANP.
Figure 5:
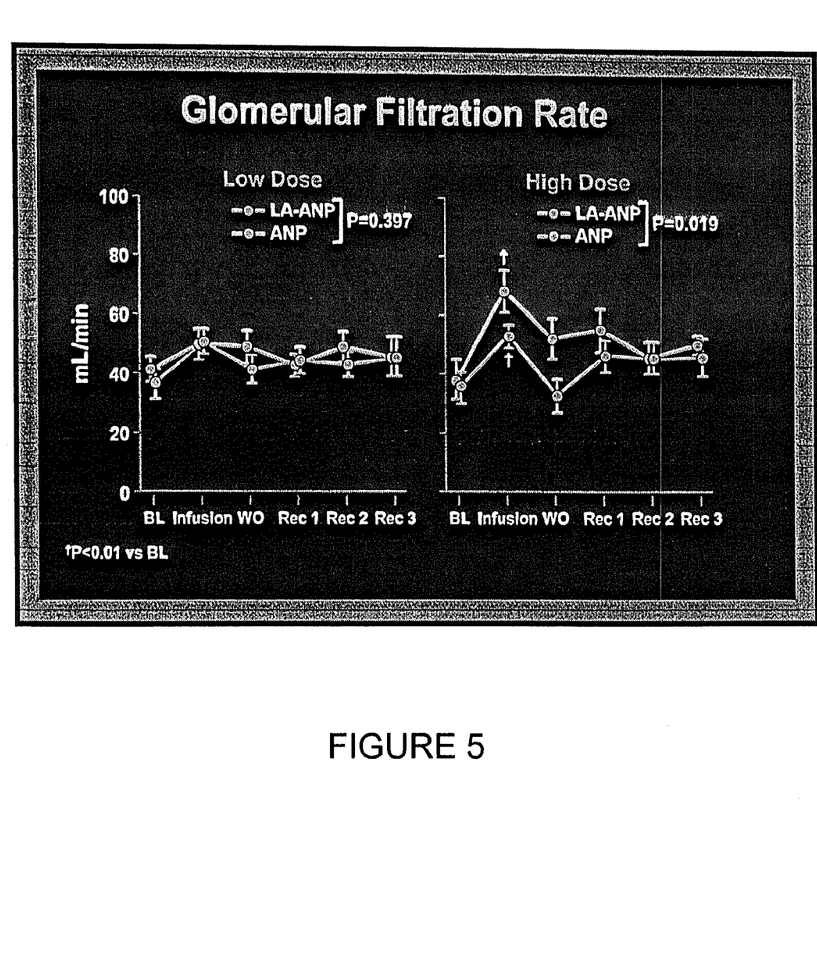
FIG. 5 is a graph plotting glomerular filtration rate at the indicated time points for animals receiving ANP or LA-ANP.
Figure 7:
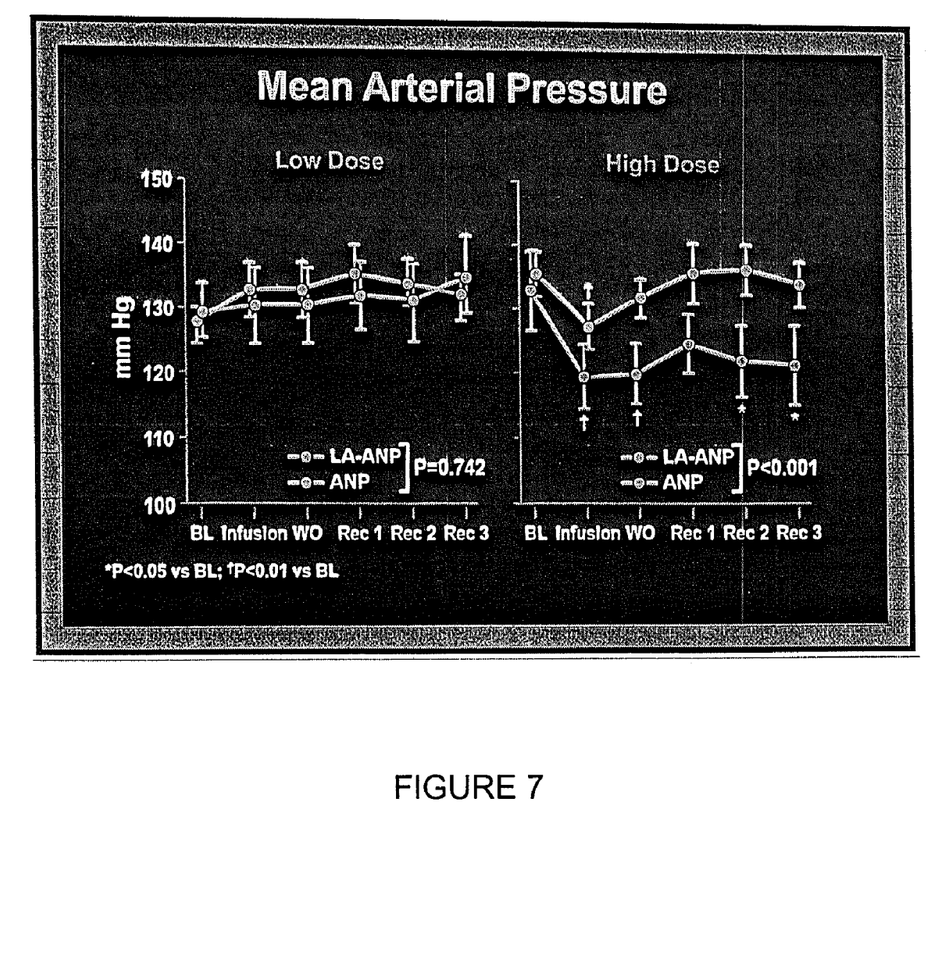
FIG. 7 is a graph plotting mean arterial pressure at the indicated time points for animals receiving ANP or LA-ANP.

The natriuretic and diuretic actions of a low dose of LA-ANP were localized to the terminal nephron where distal fractional sodium reabsorption decreased from 97.2±0.9% at baseline to 96.0±0.6% during infusion, and to 95.3±0.9% at 120 minutes post-infusion. Overall, this was significantly decreased as compared to that observed with a low dose of ANP (p<0.01). No change in glomerular filtration rate or mean arterial pressure was observed during infusion of a low dose of LA-ANP or ANP.

Figure 6:
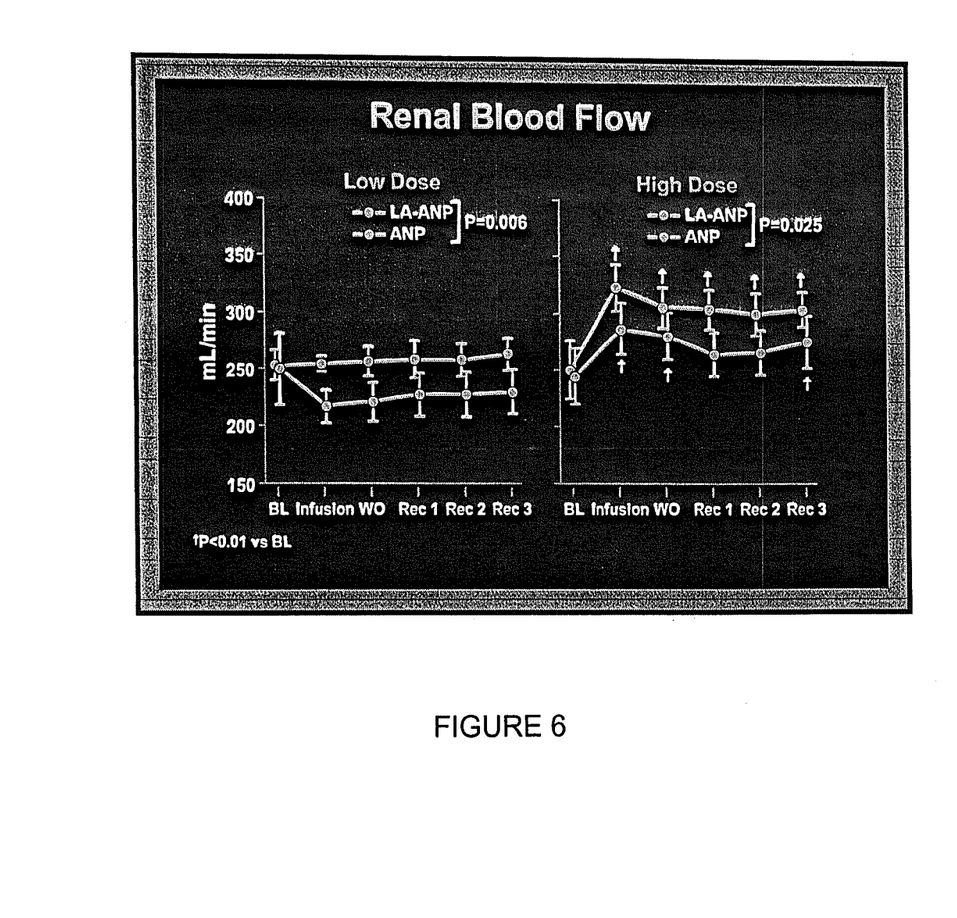
FIG. 6 is a graph plotting renal blood flow at the indicated time points for animals receiving ANP or LA-ANP.

Renal blood flow was increased during infusion of low dose LA-ANP as compared to renal blood flow during infusion of low dose ANP. Infusion of a high dose of LA-ANP increased glomerular filtration rate and decreased mean arterial pressure as compared to the effects of a high dose of ANP.

Example 2

Analysis of ANP and LA-ANP in Blood Samples

A genome-wide mapping study was performed in a family having an inherited form of atrial fibrillation. A linkage disequilibrium mapping approach was used to localize the familial atrial fibrillation gene to chromosome 1p35-p36 (20 Mb critical region). The gene encoding ANP, NPPA, was selected as a positional candidate gene based on high expression in heart atria.

A nucleic acid sequence that encodes human natriuretic peptide precursor A (Genbank Accession No. BC005893) is set forth in SEQ ID NO:6. A two base pair deletion (i.e., deletion of two adenosine nucleotides at positions 555 and 556 of SEQ ID NO:6) was identified in exon 3 of NPPA in clinically affected members of the family having an inherited form of atrial fibrillation. The two base pair deletion produced a frameshift mutation, which causes a fusion polypeptide (SEQ ID NO:7) to be expressed. The fusion polypeptide comprises ANP with an anomalous carboxy-terminus containing an additional 12 amino acids (SEQ ID NO: 1). The amino terminus of the amino acid sequence set forth in SEQ ID NO:7 contains a signal peptide sequence (SEQ ID NO:8). The amino acid sequence of a mature form of the fusion polypeptide (LA-ANP) is set forth in SEQ ID NO:2. Clinically affected family members were identified as heterozygous carriers of the frameshift mutation.

A polyclonal antibody directed against the LA-ANP polypeptide was generated using the following polypeptide: Acetyl-CYRITAREDKQGWA (SEQ ID NO:9). The antibody was used to analyze LA-ANP in blood samples from members of the family having an inherited form of atrial fibrillation. Plasma samples were collected from two family members carrying the frameshift mutation in a gene encoding ANP polypeptide, and from one family member without the mutation. Radioimmunoassays were used to measure the concentrations of ANP and LA-ANP in the sera from the family members as described below and elsewhere (Burnett et al., Science, 231:1145-1147 (1986)).

Blood was drawn into EDTA tubes and chilled until it was centrifuged at 2500 rpm for 10 minutes at 4° C. One mL aliquots of the plasma samples were placed into 12×75 mm polystyrene tubes and frozen until assayed. One mL of each plasma sample was extracted using a C-18 Bond Elut cartridge. The cartridges were washed with 4 mL of 100% methanol and 4 mL of water prior to adding the plasma samples. After applying the plasma samples to the washed cartridges, the cartridges were washed with 2 mL of saline, 6 mL of water, and 1 mL of 100% methanol. ANP polypeptides were eluted with 2 mL of a solution containing 75% methanol and 1% TFA. The eluates were concentrated and dried overnight using a Savant SpeedVac. The dried eluates were resuspended in 300 µL of assay buffer. Standards and samples (100 µL) were each incubated with 100 µL of diluted (1:150,000) anti-human ANP (Phoenix Pharmaceuticals, Mountain View, Calif.) at 4° C. After 18 hours, 100 µL (10,000 counts) of $I^{125}$-labeled ANP antibody were added, and the mixture was incubated at 4° C. for 18 hours. A second antibody was then added to each sample to separate the free and bound fractions. The samples were centrifuged, the free fraction was aspirated, and the bound fraction was counted on a gamma counter. A standard curve was generated and used to calculate the concentrations of the unknown samples, which were reported as pg/mL. The range of the standard curve was 2-500 pg/mL. The inter and intra-assay variability were 9% and 6%, respectively. The recovery of 64 pg was 81%±2%. The cross-reactivity was <1% with N-ANP, BNP, CNP, ET, and ADM. The range for normal humans was 25±11 pg/mL (n=100). A method similar to that used to analyze ANP was used to analyze LA-ANP with LA-ANP antibodies and $I^{125}$ labeled polypeptide (SEQ ID NO:9) used to generate the polyclonal LA-ANP antibody. The results of these analyses are presented in Table 1.

TABLE 1

Plasma concentrations of ANP, LA-ANP, cGMP, and BNP

| Patient | ANP pg/mL | Mutant ANP (LA-ANP) pg/mL | cGMP | BNP pg/mL |
|---|---|---|---|---|
| Affected-1* | 10.3 | 110 | 3.4 | 4 |
| Unaffected** | 11.6 | 9.7 | 2.6 | 19.4 |
| Affected-2* | 23.3 | 108 | 4 | 12.9 |
| Normal F | 2 | 13.1 | 1.1 | 4 |
| Normal F | 8.5 | 12.9 | 1.8 | 7.8 |
| Normal F | 21.9 | 13.1 | 2.4 | 12.6 |
| Normal M | 12.9 | 13 | 1.2 | 32.2 |
| Normal M | 5.4 | 13.8 | 2.8 | 16 |

*heterozygous carrier of NPPA mutation
**family member without NPPA mutation

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A substantially pure polypeptide comprising a first amino acid sequence and a second amino acid sequence, wherein said first amino acid sequence comprises the sequence of a natriuretic polypeptide having natriuresis activity, wherein said second amino acid sequence comprises the amino acid sequence as set forth in SEQ ID NO:1 or the amino acid sequence as set forth in SEQ ID NO:1 having less than five amino acid additions, subtractions, and substitutions, wherein said substantially pure polypeptide has said natriuresis activity.

2. The polypeptide of claim 1, wherein said first amino acid sequence comprises an amino acid sequence present in an ANP polypeptide.

3. The polypeptide of claim 1, wherein said first amino acid sequence comprises an amino acid sequence present in a BNP polypeptide.

4. The polypeptide of claim 1, wherein said first amino acid sequence comprises an amino acid sequence present in an CNP polypeptide.

5. The polypeptide of claim 1, wherein said first amino acid sequence comprises an amino acid sequence present in an DNP polypeptide.

6. The polypeptide of claim 1, wherein said first amino acid sequence comprises an amino acid sequence present in a salmon natriuretic factor polypeptide.

7. The polypeptide of claim 1, wherein said second amino acid sequence comprises the amino acid sequence as set forth in SEQ ID NO:1.

8. The polypeptide of claim 1, wherein said second amino acid sequence comprises the amino acid sequence as set forth in SEQ ID NO:1 having less than five amino acid additions, subtractions, and substitutions.

9. The polypeptide of claim 1, wherein said second amino acid sequence comprises the amino acid sequence as set forth in SEQ ID NO:1 having less than four amino acid additions, subtractions, and substitutions.

* * * * *

UNITED STATES PATENT AND TRADEMARK OFFICE
CERTIFICATE OF CORRECTION

| | | |
|---|---|---|
| PATENT NO. | : 7,803,901 B2 | Page 1 of 1 |
| APPLICATION NO. | : 12/065673 | |
| DATED | : September 28, 2010 | |
| INVENTOR(S) | : John C. Burnett, Jr. | |

It is certified that error appears in the above-identified patent and that said Letters Patent is hereby corrected as shown below:

Column 1, line 14, insert:

--STATEMENT AS TO FEDERALLY SPONSORED RESEARCH
This invention was made with government support under grant no. HL36634, awarded by the National Institutes of Health. The government has certain rights in the invention.--

Signed and Sealed this
First Day of January, 2013

David J. Kappos
*Director of the United States Patent and Trademark Office*

SEQUENCE LISTING

<160> NUMBER OF SEQ ID NOS: 9

<210> SEQ ID NO 1
<211> LENGTH: 12
<212> TYPE: PRT
<213> ORGANISM: Homo sapiens

<400> SEQUENCE: 1

Arg Ile Thr Ala Arg Glu Asp Lys Gln Gly Trp Ala
1               5                   10

<210> SEQ ID NO 2
<211> LENGTH: 40
<212> TYPE: PRT
<213> ORGANISM: Homo sapiens

<400> SEQUENCE: 2

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Gly Trp Ala
        35                  40

<210> SEQ ID NO 3
<211> LENGTH: 28
<212> TYPE: PRT
<213> ORGANISM: Homo sapiens

<400> SEQUENCE: 3

Ser Leu Arg Arg Ser Ser Cys Phe Gly Gly Arg Met Asp Arg Ile Gly
 1               5                  10                  15

Ala Gln Ser Gly Leu Gly Cys Asn Ser Phe Arg Tyr
            20                  25

<210> SEQ ID NO 4
<211> LENGTH: 93
<212> TYPE: DNA
<213> ORGANISM: Homo sapiens

<400> SEQUENCE: 4
agcctgcgga gatccagctg cttcgggggc aggatggaca ggattggagc ccagagcgga      60
ctgggctgta acagcttccg gtaccgaaga taa                                  93

<210> SEQ ID NO 5
<211> LENGTH: 123
<212> TYPE: DNA
<213> ORGANISM: Homo sapiens

<400> SEQUENCE: 5
agcctgcgga gatccagctg cttcgggggc aggatggaca ggattggagc ccagagcgga      60
ctgggctgta acagcttccg gtaccggata acagccaggg aggacaagca gggctgggcc     120
tag                                                                  123

<210> SEQ ID NO 6
<211> LENGTH: 883
<212> TYPE: DNA
<213> ORGANISM: Homo sapiens

<400> SEQUENCE: 6
gagacaggga cagacgtagg ccaagagagg ggaaccagag aggaaccaga ggggagagac      60
agagcagcaa gcagtggatt gctccttgac gacgccagca tgagctcctt ctccaccacc     120
accgtgagct tcctcctttt actggcattc cagctcctag gtcagaccag agctaatccc     180
atgtacaatg ccgtgtccaa cgcagacctg atggatttca gaatttgct ggaccatttg      240 gaagaaaaga tgcctttaga agatgaggtc gtgccccac aagtgctcag tgagccgaat      300
gaagaagcgg gggctgctct cagccccctc cctgaggtgc ctccctggac cggggaagtc     360
agcccagccc agagagatgg aggtgccctc gggcggggcc cctgggactc ctctgatcga     420
tctgccctcc taaaaagcaa gctgagggcg ctgctcactg cccctcggag cctgcggaga     480
tccagctgct tcggggggcag gatggacagg attggagccc agagcggact gggctgtaac     540
agcttccggt accgaagata acagccaggg aggacaagca gggctgggcc tagggacaga     600
ctgcaagagg ctcctgtccc ctgggtctc tgctgcattc gtgtcatctt gttgccatgg      660
agttgtgatc atcccatcta agctgcagct tcctgtcaac acttctcaca tcttatgcta     720
actgtagata aagtggtttg atggtgactt cctcgcctct cccacccccat gcattaaatt    780 ttaaggtaga acctcacctg ttactgaaag tggtttgaaa gtgaataaac ttcagcacca     840
tggacagaag accaaaaaaa aaaaaaaaa aaaaaaaaaa aaa                        883

<210> SEQ ID NO 7
<211> LENGTH: 163
<212> TYPE: PRT
<213> ORGANISM: Homo sapiens

```
<400> SEQUENCE: 7

Met Ser Ser Phe Ser Thr Thr Thr Val Ser Phe Leu Leu Leu Leu Ala
 1               5                  10                  15

Phe Gln Leu Leu Gly Gln Thr Arg Ala Asn Pro Met Tyr Asn Ala Val
             20                  25                  30

Ser Asn Ala Asp Leu Met Asp Phe Lys Asn Leu Leu Asp His Leu Glu
             35                  40                  45

Glu Lys Met Pro Leu Glu Asp Glu Val Val Pro Pro Gln Val Leu Ser
         50                  55                  60

Glu Pro Asn Glu Glu Ala Gly Ala Ala Leu Ser Pro Leu Pro Glu Val
65                   70                  75                  80

Pro Pro Trp Thr Gly Glu Val Ser Pro Ala Gln Arg Asp Gly Gly Ala
                 85                  90                  95

Leu Gly Arg Gly Pro Trp Asp Ser Ser Asp Arg Ser Ala Leu Leu Lys
                100                 105                 110

Ser Lys Leu Arg Ala Leu Leu Thr Ala Pro Arg Ser Leu Arg Arg Ser
            115                 120                 125

Ser Cys Phe Gly Gly Arg Met Asp Arg Ile Gly Ala Gln Ser Gly Leu
            130                 135                 140

Gly Cys Asn Ser Phe Arg Tyr Arg Ile Thr Ala Arg Glu Asp Lys Gln
145                 150                 155                 160

Gly Trp Ala

<210> SEQ ID NO 8
<211> LENGTH: 25
<212> TYPE: PRT
<213> ORGANISM: Homo sapiens

<400> SEQUENCE: 8

Met Ser Ser Phe Ser Thr Thr Thr Val Ser Phe Leu Leu Leu Leu Ala
 1               5                  10                  15

Phe Gln Leu Leu Gly Gln Thr Arg Ala
             20                  25

<210> SEQ ID NO 9
<211> LENGTH: 14
<212> TYPE: PRT
<213> ORGANISM: Homo sapiens
<220> FEATURE:
<221> NAME/KEY: MOD_RES
<222> LOCATION: 1
<223> OTHER INFORMATION: Xaa = acetylcysteine

<400> SEQUENCE: 9

Xaa Tyr Arg Ile Thr Ala Arg Glu Asp Lys Gln Gly Trp Ala
 1               5                  10
```